United States Patent [19]

Kitada

[11] Patent Number: 6,087,516
[45] Date of Patent: Jul. 11, 2000

[54] PROCESS FOR PRODUCING BIS (1,2-ETHANEDIAMINE) GOLD CHLORIDE AND GOLD-PLATING SOLUTION CONTAINING THE GOLD CHLORIDE

[75] Inventor: Katsutsugu Kitada, Chigasaki, Japan

[73] Assignee: Tanaka Kikinzoku Kogyo K.K., Japan

[21] Appl. No.: 09/371,133

[22] Filed: Aug. 10, 1999

[51] Int. Cl.[7] ........................................................ C07F 1/12
[52] U.S. Cl. ........................... 556/110; 106/1.23; 106/1.26
[58] Field of Search ............................ 556/110; 106/1.23, 106/1.26

[56] References Cited

PUBLICATIONS

B.P. Block et al., "The Reaction of Gold(III) With Some Bidentate Coördinating Groups", J. Am. Chem. Soc., vol. 73, pp. 4722–4725, 1951.

*Primary Examiner*—Porfirio Nazario-Gonzalez
*Attorney, Agent, or Firm*—Arent Fox Kintner Plotkin & Kahn

[57] ABSTRACT

The present invention provides a process for producing bis(1,2-ethanediamine)gold chloride at high yield within a short reaction time and allows use of a safe solvent, as well as a gold-plating solution containing the gold chloride. Bis(1,2-ethanediamine)gold chloride can be produced at high yield through reaction of sodium chloroaurate and ethylenediamine anhydrate by use of a solvent. According to one characteristic feature of the process of the present invention, a safe solvent; i.e., at least one of acetonitrile, methanol, and ethanol, is used.

20 Claims, No Drawings

PROCESS FOR PRODUCING BIS (1,2-ETHANEDIAMINE) GOLD CHLORIDE AND GOLD-PLATING SOLUTION CONTAINING THE GOLD CHLORIDE

BACKGROUND OF THE INVENTION

1. Field of the Invention

The present invention relates to a process for producing bis(1,2-ethanediamine)gold chloride, as well as to a gold-plating solution containing the gold chloride.

2. Background Art

Gold plating, which has long been performed in the fields of decorations and tableware, is widely used in the electronics industry due to the excellent electrical properties of gold.

In most cases, a cyan bath containing toxic potassium cyanoaurate has generally been employed as a gold-plating solution. However, there has recently arisen increased demand for a cyan-free gold-plating solution, in view of problems resulting from use of a cyan bath, such as concerns of safety at work sites, wastewater treatment, or attack of resists of semiconductor elements.

With regard to a cyan-free gold-plating solution, *J. Am. Chem. Soc.*, 1951, vol. 73, p4722 discloses a plating solution containing bis(1,2-ethanediamine)gold chloride as a gold compound. According to this literature, bis(1,2-ethanediamine)gold chloride is obtained through reaction of chloroauric acid and ethylenediamine monohydrate in a solvent, diethyl ether, at ambient temperature.

However, such a conventional process provides a limited yield of bis(1,2-ethanediamine)gold chloride; i.e., a yield of about 73% at most. In addition, diethyl ether used in the process is a solvent involving a problem in safety.

SUMMARY OF THE INVENTION

In view of the foregoing, an object of the present invention is to provide a process for producing bis(1,2-ethanediamine)gold chloride which provides a high yield and permits use of a less toxic solvent. Another object of the present invention is to provide a gold-plating solution containing the gold chloride.

The present inventors have conducted earnest studies on a variety of starting materials in order to develop a more practical process for producing bis(1,2-ethanediamine)gold chloride, and have found that when sodium chloroaurate is reacted with ethylenediamine anhydrate in a solvent, bis(1,2-ethanediamine)gold chloride can be produced at high yield. The present invention has been accomplished based on this finding.

Accordingly, in a first aspect of the present invention, there is provided a process for producing bis(1,2-ethanediamine)gold chloride in which sodium chloroaurate and ethylenediamine anhydrate are reacted at 15–60° C. by use of a solvent.

Preferably, the solvent is a safe solvent, and may be at least one of acetonitrile, methanol, and ethanol.

In a second aspect of the present invention, there is provided a gold-plating solution containing the thus-obtained bis(1,2-ethanediamine)gold chloride and sodium bromide and having a pH of 1–8.

Preferably, the concentration of bis(1,2-ethanediamine)gold chloride is 0.01–0.2 M and that of sodium bromide is 0.01–1 M.

The gold-plating solution preferably contains a thallium compound and/or a lead compound in an amount of 0.1–50 ppm.

DETAILED DESCRIPTION OF PREFERRED EMBODIMENTS

The reaction between sodium chloroaurate ($NaAuCl_4$) and ethylenediamine anhydrate is expressed as follows.

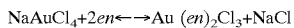

$$NaAuCl_4 + 2en \leftrightarrow Au(en)_2Cl_3 + NaCl$$

According to the present invention, the reaction temperature is 15–60° C. When the temperature is less than 15° C., the reaction proceeds insufficiently to thereby reduce the yield; whereas when it is in excess of 60° C., gold ions are reduced to thereby form microparticles of gold. The process according to the present invention provides the target compound at a yield of 90% through a reaction time of about one hour. The high yield is attributed to dissociation of ethylenediamine being prevented due to a low content of water in the synthesis system.

By use of the thus-obtained bis(1,2-ethanediamine)gold chloride, a bath of a gold-plating solution can be prepared. The gold-plating solution comprises bis(1,2-ethanediamine) gold chloride and sodium bromide as essential components and has a pH of 1–8.

Bis(1,2-ethanediamine)gold chloride is preferably contained in the gold-plating solution at a concentration of 0.01–0.2 M. Most preferable concentration of sodium bromide is 0.01–1 M. Sodium bromide supplies bromide ions serving as a counter ion of the bis(1,2-ethanediamine)gold complex and functions as a stabilizer. As described above, the pH of the plating solution must fall within the range between 1 and 8. When the pH falls outside this range, the appearance of the obtained plating and the stability of the plating solution degrade.

In other words, the reactions as described below occur under the above-described conditions, and the resultant gold complex represented by [Au(en)(en-H)Br] provides gold plating of excellent appearance and enhances stability of the plating solution.

$$Au(en)_2Cl_3 + 3NaBr \rightarrow Au(en)_2Br_3$$

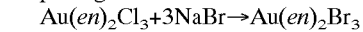

$$Au(en)_2Br_3 \leftrightarrow Au(en)(en\text{-}H)Br$$

In order to enhance the deposition rate of gold, a thallium compound and/or a lead compound may be added as metal to the gold-plating solution at a concentration of 0.1–50 ppm. Examples of preferred thallium compounds include thallium acetate, thallium formate, thallium sulfate, thallium oxide, thallium malonate, and thallium chloride. Of these, thallium formate is easily handled due to its low toxicity. Examples of suitable lead compounds include lead citrate, lead acetate, and lead oxide.

In the present invention, no particular limitation is imposed on the current density and temperature of the gold-plating solution. Also, the gold-plating solution of the present invention is applicable not only to immersion plating but also to jet plating.

The present invention will next be described in detail by way of examples.

EXAMPLES

Firstly, a process for synthesizing bis(1,2-ethanediamine) gold chloride will be described. In working examples of the present invention (Nos. 1 through 3), $NaAuCl_4$ (50.8 mmol) was dissolved in a solvent (100 ml) to thereby form a solution, and ethylenediamine anhydrate (107 mmol) was gradually added to the solution. The mixture was allowed to react at 60° C. for one hour with stirring. The precipitate was separated by filtration, washed with EtOH (200 ml), and dissolved in deionized water (100 ml). To the solution, EtOH (500 ml) was added to thereby precipitate again. The resultant precipitate was dried to thereby obtain a target compound. In comparative examples (Nos. 4 through 6), a similar synthesis was performed except that $HAuCl_4$ and ethylenediamine monohydrate were used as the starting materials and diethyl ether ($Et_2O$) was used as a solvent.

The yields of the bis(1,2-ethanediamine)gold chloride obtained from working examples of the present invention (Example Nos. 1 through 3) and comparative examples (Nos. 4 through 6) are shown in Table 1. As is clear from Table 1, the yield is higher in the cases of working examples of the present invention (Nos. 1 through 3) employing $NaAuCl_4$ than in comparative examples (Nos. 4 through 6) employing $HAuCl_4$.

TABLE 1

| No. | Au Complex | Ethylene-diamine | Solvent | Reaction | Reaction time | Yield |
|---|---|---|---|---|---|---|
| 1 | $NaAuCl_4$ (50.8 mmol) | en anhydrate (107 mmol) | MeCN (100 ml) | 60° C., stirring | 1 hr | 90% |
| 2 | $NaAuCl_4$ (50.8 mmol) | en anhydrate (107 mmol) | MeOH (100 ml) | 60° C., stirring | 1 hr | 90% |
| 3 | $NaAuCl_4$ (50.8 mmol) | en anhydrate (107 mmol) | EtOH (100 ml) | 60° C., stirring | 1 hr | 90% |
| 4 | $HAuCl_4$ (50.8 mmol) | en mono-hydrate (107 mmol) | $Et_2O$ (100 ml) | ambient temp., stirring | 1 hr | 55% |
| 5 | $HAuCl_4$ (50.8 mmol) | en mono-hydrate (107 mmol) | $Et_2O$ (100 ml) | ambient temp., stirring | 1 hr | 15% |
| 6 | $HAuCl_4$ (50.8 mmol) | en mono-hydrate (107 mmol) | $Et_2O$ (100 ml) | reflux | 1 hr | 73% |

By use of the thus-synthesized bis(1,2-ethanediamine) gold chloride, gold-plating solution baths formulated as shown in Table 2 were prepared. Gold plating was performed by use of a Pt/Ti anode and a cathode formed of a copper panel electroplated with Ni so as to have a Ni thickness of 2 μm.

TABLE 2

| Components & conditions | EXAMPLE No. | | |
|---|---|---|---|
| | 1 | 2 | 3 |
| $Au(en)_2Cl_3$ | 0.05M | 0.05M | 0.05M |
| en $H_2SO_4$ | 2M | 2M | 2M |
| NaBr | 1M | 1M | 2M |
| $CH_3COOTl$ | 6 ppm | 12 ppm | 12 ppm |
| pH | 6.5 | 6.5 | 6.5 |
| Temperature | 60° C. | 60° C. | 60° C. |
| Anodic c.d. (A/dm²) | 0.5 | 1.0 | 1.5 |
| Deposition rate (mg/A min) | 40 | 40 | 40 |
| Appearance (color) | lemon yellow | lemon yellow | lemon yellow |

As shown in Table 2, all the plating baths produced gold plating of excellent appearance. The deposition rate was satisfactory, and the baths were stable during plating.

As disclosed hereinabove, the process according to the present invention attains synthesis of bis(1,2-ethanediamine) at high yield and allows use of a safe solvent. The gold-plating solution containing the obtained bis(1,2-ethanediamine) provides a plating film having a lemon yellow gloss. In addition, the plating solution has excellent stability and a long service life. Since the plating solution contains no cyan species, it involves no problem regarding work-site safety and no adverse environmental effects.

What is claimed is:

1. A process for producing bis(1,2-ethanediamine)gold chloride in which sodium chloroaurate and ethylenediamine anhydrate are reacted at 15–60° C. by use of a solvent.

2. The process according to claim 1, wherein the solvent is at least one member selected from among acetonitrile, methanol, and ethanol.

3. A gold-plating solution comprising bis(1,2-ethanediamine)gold chloride obtained through the process as defined in claim 1 and sodium bromide and having a pH of 1–8.

4. A gold-plating solution comprising bis(1,2-ethanediamine)gold chloride obtained through the process as defined in claim 2 and sodium bromide and having a pH of 1–8.

5. The gold-plating solution according to claim 3, wherein the concentration of bis(1,2-ethanediamine)gold chloride is 0.01–0.2 M.

6. The gold-plating solution according to claim 4, wherein the concentration of bis(1,2-ethanediamine)gold chloride is 0.01–0.2 M.

7. The gold-plating solution according to claim 3, wherein the concentration of sodium bromide is 0.01–1 M.

8. The gold-plating solution according to claim 4, wherein the concentration of sodium bromide is 0.01–1 M.

9. The gold-plating solution according to claim 3, wherein a thallium compound and a lead compound is contained at a concentration of 0.1–50 ppm.

10. The gold-plating solution according to claim 3, wherein a thallium compound or a lead compound is contained at a concentration of 0.1–50 ppm.

11. The gold-plating solution according to claim 4, wherein a thallium compound and a lead compound is contained at a concentration of 0.1–50 ppm.

12. The gold-plating solution according to claim 4, wherein a thallium compound or a lead compound is contained at a concentration of 0.1–50 ppm.

13. The gold-plating solution according to claim 5, wherein a thallium compound and a lead compound is contained at a concentration of 0.1–50 ppm.

14. The gold-plating solution according to claim 5, wherein a thallium compound or a lead compound is contained at a concentration of 0.1–50 ppm.

15. The gold-plating solution according to claim 6, wherein a thallium compound and a lead compound is contained at a concentration of 0.1–50 ppm.

16. The gold-plating solution according to claim 6, wherein a thallium compound or a lead compound is contained at a concentration of 0.1–50 ppm.

17. The gold-plating solution according to claim 7, wherein a thallium compound and a lead compound is contained at a concentration of 0.1–50 ppm.

18. The gold-plating solution according to claim 7, wherein a thallium compound or a lead compound is contained at a concentration of 0.1–50 ppm.

19. The gold-plating solution according to claim 8, wherein a thallium compound and a lead compound is contained at a concentration of 0.1–50 ppm.

20. The gold-plating solution according to claim 8, wherein a thallium compound or a lead compound is contained at a concentration of 0.1–50 ppm.

* * * * *